United States Patent

Turner et al.

[11] Patent Number: 5,091,299
[45] Date of Patent: Feb. 25, 1992

[54] AN ENZYME ELECTRODE FOR USE IN ORGANIC SOLVENTS

[76] Inventors: Anthony P. F. Turner, Evergreens, Bourne End Road, Cranfield, Bedfordshire, MK43 OBD, England; David J. Best, Whingarth, Gunnerton, Hexham, Northumberland, England; Geoffrey F. Hall, 112 High Street, Cranfield, Bedfordshire, MK43 ODG, England

[21] Appl. No.: 543,746

[22] PCT Filed: Nov. 10, 1988

[86] PCT No.: PCT/GB88/00970
§ 371 Date: Jul. 12, 1990
§ 102(e) Date: Jul. 12, 1990

[87] PCT Pub. No.: WO89/04364
PCT Pub. Date: May 18, 1989

[30] Foreign Application Priority Data

Nov. 13, 1987 [GB] United Kingdom ............ 8726574
Apr. 21, 1988 [GB] United Kingdom ............ 8809485

[51] Int. Cl.$^5$ .................. G01N 27/26; C12M 1/40; C12Q 1/00
[52] U.S. Cl. .................. 435/4; 435/288; 435/817; 204/403
[58] Field of Search .......... 204/403; 435/817, 288

[56] References Cited

U.S. PATENT DOCUMENTS

| | | | |
|---|---|---|---|
| 4,145,255 | 3/1979 | Schiller et al. | 435/817 |
| 4,224,125 | 9/1980 | Nakamura et al. | 435/817 |
| 4,556,635 | 12/1985 | Hitzman et al. | 435/817 |

FOREIGN PATENT DOCUMENTS 214336 3/1987 European Pat. Off. .

OTHER PUBLICATIONS

Kazand Jian et al., J. Am. Chem. Soc. 107, 5448–5450, 1985.

Primary Examiner—David L. Lacey
Assistant Examiner—William K. Y. Chan
Attorney, Agent, or Firm—Larson and Taylor

[57] ABSTRACT

A method of determining an analyte in an organic or microaqueous solution involves the use of an enzyme electrode at which an enzyme is retained. The enzyme may be immobilised covalently at the electrode but is preferably retained at a hydrophilic support (4) which may be connected to an electrical conductor. Electrochemical detection of analytes in organic or microaqueous solvents using an enzyme electrode has several advantages over existing methods which employ aqueous solutions of analyte. For example compounds with low water solubilities may be detected, detection of a particular analyte may be made more selective by appropriate choice of solvent, the thermal stability of the enzyme may be enhanced and the enzymes may be readily retained at the electrode by virtue of their insolubility in the organic or microaqueous solvent.

16 Claims, 2 Drawing Sheets

AN ENZYME ELECTRODE FOR USE IN ORGANIC SOLVENTS

TECHNICAL FIELD

The present invention relates to bioelectrochemical reactions carried out in non-aqueous or microaqueous solvents. A microaqueous solvent is one formed by the addition of small quantities of water to a non-aqueous solvent (Yamane et al, 1988) and as used herein the term includes water-immiscible solvents which are saturated with water.

In particular, the present invention relates to a method of carrying out a bioelectrochemical reaction in a non-aqueous or microaqueous solution, the use of such a method for the determination of an analyte, and to an electrochemical cell and an enzyme electrode for carrying out such methods.

BACKGROUND ART

It is well kown to employ an enzyme electrode in order to perform and monitor a bioelectrochemical reacton in aqueous solution. For example, an enzyme electrode involving glucose oxidase may be used to effect the oxidaton of glucose, and consequently to monitor the concentration of glucose in aqueous solution (see e.g. Turner et al, 1985). In such electrodes the enzyme is, conventionally, immobilised on the electrode by means of covalent bonding, and electron transfer between the redox centre of the enzyme and the electrode surface may be effected by means of a mediator molecule such as ferrocene (Cass et al 1984)

The use of enzyme electrodes in aqueous solutions enables the concentration of chemical substances in samples to be determined without extensive preparation. The enzyme provides the specificity of a biochemical reaction and the electrode monitors the extent or progress of the reaction in a sensitive manner (Turner et al, 1987).

However, the methods used to date suffer from several disadvantages. For example, the method is limited to the determination of species which are relatively water soluble, the electrode material must be one which is stable and operable in an aqueous solvent, and the method is not appropriate for use at elevated temperatures because of poor thermal stability of many enzymes in aqueous environments.

The present inventors have found that it is possible to carry out bioelectrochemical reactions in organic or microaqueous solvents. Although enzyme reactions in organic and microaqueous solvents have been reported (Klibanov, 1986; Halling, 1987; Kazandijan et al, 1985) the possibility of employing enzyme electrodes in organic electrochemisty has not, previously, been explored.

DISCLOSURE OF THE INVENTION

According to one aspect of the present invention there is provided a method for carrying out a bioelectrochemical reaction in a non-aqueous or microaqueous solvent, the method comprising contacting a non-aqueous or microaqueous solution of a substrate for an enzyme with an electrode at which said enzyme is retained and allowing the substrate to undergo reaction at the electrode under the influence of said enzyme. One possibility is that the enzyme catalyses the conversion of the substrate into a porduct which then undergoes an electrochemical reaction directly at the electrode. An alternative is that the enzyme is one which can effect oxidation or reduction of the substrate, possibly with the intervention of a mediator, and is thus involved in the transfer of electrons between the substrate and the electrode. The enzyme may be present as a component of a whole cell, cell membrane, or organelle, or as a purified substance.

By carrying out the bioelectrochemical reaction in non-aqueous or microaqueous solvent the enzyme specificity may be made different from that in aqueous solution and the possibility exists of selecting particular specificities by making an appropriate choice of non-aqueous solvent. Furthermore, the solvent may be chosen so as to stabilise the enzyme substrate or product and hence enable the observation of otherwise difficult electrochemistry. Since thermal stability of enzymes is often enhanced in non-aqueous solvents reactions may also be carried out at elevated temperatures.

The method may be employed in the determination of an analyte in non-aqueous or microaqueous solution by including a non-aqueous or microaqueous solution to be analysed for said analyte in an electrochemical cell, said cell having an electrode at which an enzyme is retained; and by measuring an electrical response of said cell.

There are various possible analytes which might be detected. Principally, these are enzyme substrates or cofactors for said enzyme; redox species capable of mediating electron transfer with the enzyme of the electrode; or substances convertible to any of these. Analytes of low water solubility may now be determined for example by concentrating analyte from a large volume of water into a smaller quantity of non-aqueous solvent, for example by countercurrent chromatography. Thus, for instance, organic substances such as phenols which may occur in low concentration in the water supply may be readily determined by extraction into chloroform.

It is thought that in order for an enzyme to operate in non-aqueous or microaqueous solution a very low concentration of water should be distributed over the surface of the enzyme. Although the role of the water molecules around the enzyme is not fully understood it is believed that the water is necessary for the retention of the enzyme's structure. This places some limitations on the non-aqueous solvents which may be used when carrying out bioelectrochemistry. The solvent should not be so polar that it removes essential water from the enzyme. The solvent will, generally, be organic and hydrophobic solvents such as hydrocarbons are particularly suitable. Other solvents which are more hydrophilic but still water immiscible such as organic halides (of which chloroform is a preferred example), ethers and esters may be used but are preferably saturated with water. Mixtures of any of the above may be used. Non-aqueous solvents which are capable of dissolving enzymes are best avoided.

A further aspect of the present invention is an electrochemical cell for carrying out either of the methods referred to above, the cell comprising an electrode at which an enzyme is retained and containing a non-aqueous or microaqueous solvent.

The electrode utilised in the methods or cell mentioned above may have an enzyme covalently immobilised on it as is conventional in the art. However, the present invention also provides an enzyme electrode for use in a non-aqueous or microaqueous solvent, said electrode comprising a conductor, a hydrophilic support associated with the conductor and an enzyme retained at the support. Preferably, the enzyme is not covalently bound to the support but remains in proximity to it by virtue of the common hydrophilicity of the enzyme and of the support. Thus, the need for conventional enzyme immobilisation e.g. covalent attachment is avoided. Such electrodes are preferably used in conjunction with microaqueous solvents since the addition of a small quantity of water to the non-aqueous medium ensures retention and stability of the enzyme so that the enzyme electrode may, under suitable conditions, be reused several times.

The conductor with which the hydrophilic support is associated may, for example, be provided by a graphite block or might be on a microstructured electrode (for examples of which see Murray et al (1987)).

The hydrophilic support may be a membrane of a polymeric compound which contains polar residues. The polymeric compound should be one which remains stable in the organic solvent in conjunction with which the enzyme electrode is to be used. Possible polymers include nitrocellulose, cellulose acetate, polyacrylamide and nylon. Nylon is a preferred material.

Alternatively the hydrophilic support may be an inorganic membrane with polar groups at its surface which is thus hydrophilic. For example anodised aluminium membranes such as those sold under the trade name Anopore by Anotech Separations Ltd are suitable. Such membranes may be associated with a conductor to form an enzyme electrode. Another possibility is that a hydrophilic support may be formed on the surface of the conductor e.g. where the conductor is aluminium and is provided with an anodised surface.

Another aspect of the present invention is an electrochemical cell comprising an enzyme electrode for use in an organic or microaqueous solvent said electrode comprising a conductor hydrophilic support associated with the conductor and an enzyme retained at said support.

In certain embodiments of the invention a polyphenol oxidase enzyme immobilised at an electrode is employed to detect a phenol as analyte. However, other possible enzymes and analytes may be envisaged.

BREIF DESCRIPTION OF THE DRAWINGS

An embodiment of the enzyme electrode of the present invention and of its use will now be exemplified with reference to the accompanying drawings of which FIGS. 1a and 1b respectively show the construction of an electrode and the shape of wire required for electrode construction.

BEST MODE OF CARRYING OUT THE INVENTION

Figure 1A:
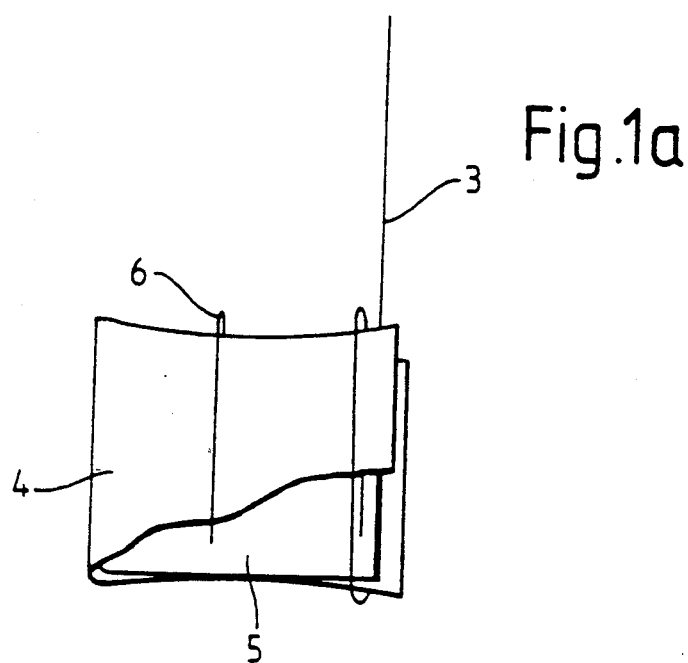

In the description which follows the enzyme polyphenol oxidase is employed to effect the oxidation of phenols in chloroform solution. Phenols may be partitioned from a large volume of water into a small volume of organic solvent, where they can be rapidly detected through reaction with an enzyme electrode. This provides a method for the determination of low concentrations of phenol in water.

ELECTRODE CONSTRUCTON

Polyphenol oxidase (1.7 mg tyrosinase from Sigma, Poole, Dorset GB) was dissolved in sodium phosphate buffer (15 µl, 50 mM, pH 7.0). This solutuion was allowed to soak into a rectangle 4(5 × 14 mm) of 'Hybond-N' nylon membrane (Amersham International plc, Little Chalfont, Bucks GB.) and left to dry for 1 h at room temperature. The membrane 4 is shown partly cut away in FIG. 1a. A length of bare nickel-chromium wire 3 was folded as in FIG. 1b. One end of the dry nylon membrane 4 was clamped into fold 1 of the length of wire 3. The membrane 4 was then folded around a block of graphite foil 5(5 × 6 × 1 mm, Le Carbone, Portslade, Sussex (GB)) which had been soaking in a solution of tetrabutylammonium tolune-4-sulfonate (TBATS) (0.1 M, Fluka, Fluorochem Ltd., Glossop, Derbyshire (GB)) in HPLC grade chloroform for at least 1 h. All chloroform used in this work had been previously saturated with sodium phosphate buffer (50 mM, pH 7.0). One of the shorter edges of the graphite foil block 5 and the unclamped end of the nylon membrane 4 were clamped into fold 2 of the wire. A length (10 mm) of nickel-chromium wire 6 was clamped around the graphite block 5 and membrane 4 to hold the membrane 4 in close contact with the graphite 5. The enzyme electrode is shown in FIG. 1a.

ELECTROCHEMICAL CELL CONSTRUCTION

Figure 1B:
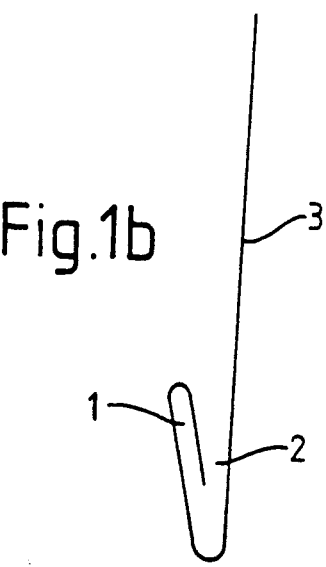
Figure 2:
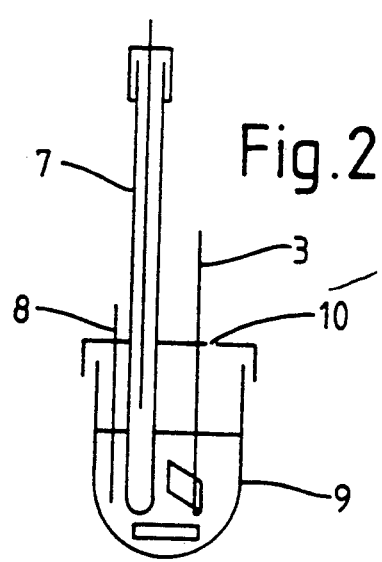
FIG. 2 shows an electrochemical cell with the enzyme electrode of FIG. 1 in place.

An electrochemical cell which includes the enzyme electrode of FIG. 1a is shown at FIG. 2. A three electrode system was employed for all work with the enzyme electrode. The potential was maintained by a precision potentiostat (Ministat. Thompson and Associates, Newcastle upon Tyne (GB). ) and the current was recorded on an x-t chart recorder (Gallenkamp, Loughborough, Leicestershire (GB).) via a resistance board (J. J. Junior, J. J. Instruments, Southampton, Herts (GB).) A capacitor (47 µF) was connected across the input terminals of the chart recorder to smooth any background noise. The potentiostat, chart recorder, resistance board and capacitor are not shown FIG. 2.

A saturated calomel electrode 7 (Russel pH Ltd., Auchtermuchty, Fife, Scotland) was used as a reference and the auxiliary electrode 8 was a platinum wire (0.4 mm diameter). The electrodes were immersed in chloroform (5 ml, 0.1 M TBATS) contained in a truncated boiling tube 9. The enzyme electrode was poised at −275 mV versus saturated calomel electrode 7 in chloroform and additions of small volumes of stock p-cresol (90 mM) in chloroform (0.1 M TBATS) were made via a small hole 10 in the lid of the electrochemical cell.

CALIBRATION OF THE ENZYME ELECTRODE

Figure 3:
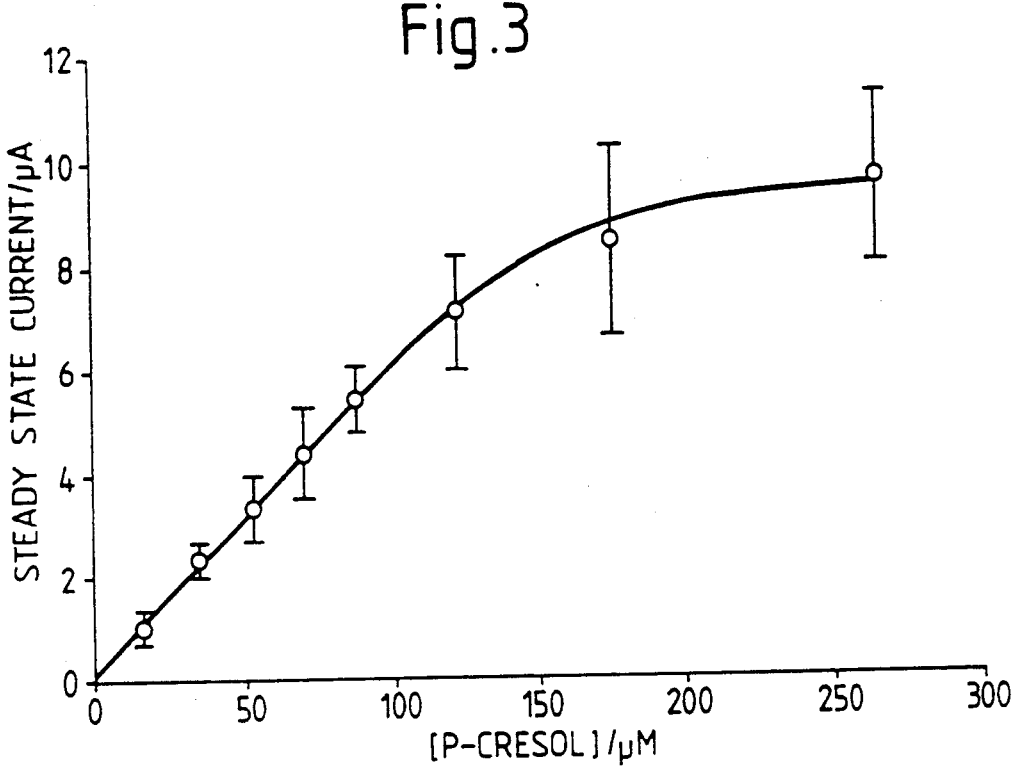
FIG. 3 is the calibration curve of the enzyme electrode for p-cresol.

Nine discrete assays were performed over a range of p-cresol concentrations (0 to 267 µM) on five different electrodes. Before each assay sodium phosphate buffer (2 µl, 50 mM, pH 7.0) was placed onto each side of the enzyme electrode to rehydrate the polyphenol oxidase. The electrode was placed into the cell described above and poised at −275 mV vs standard calomel electrode 7 in chloroform. After 25 minutes the current became constant and an addition of p-cresol was made. An increase in current was then observed which reached a steady value, typically after 3 to 5 minutes. The cell was stirred throughout each assay. After each assay the electrode was removed from the cell and washed in chloroform for about 60 secs before being dried in air prior to the next assay. The response of the electrode to p-cresol was linear in the concentration range 0–100 μM (FIG. 3). The standard error bars represent the good reproducibility between electrodes.

OPERATIONAL STABILITY

Figure 4:
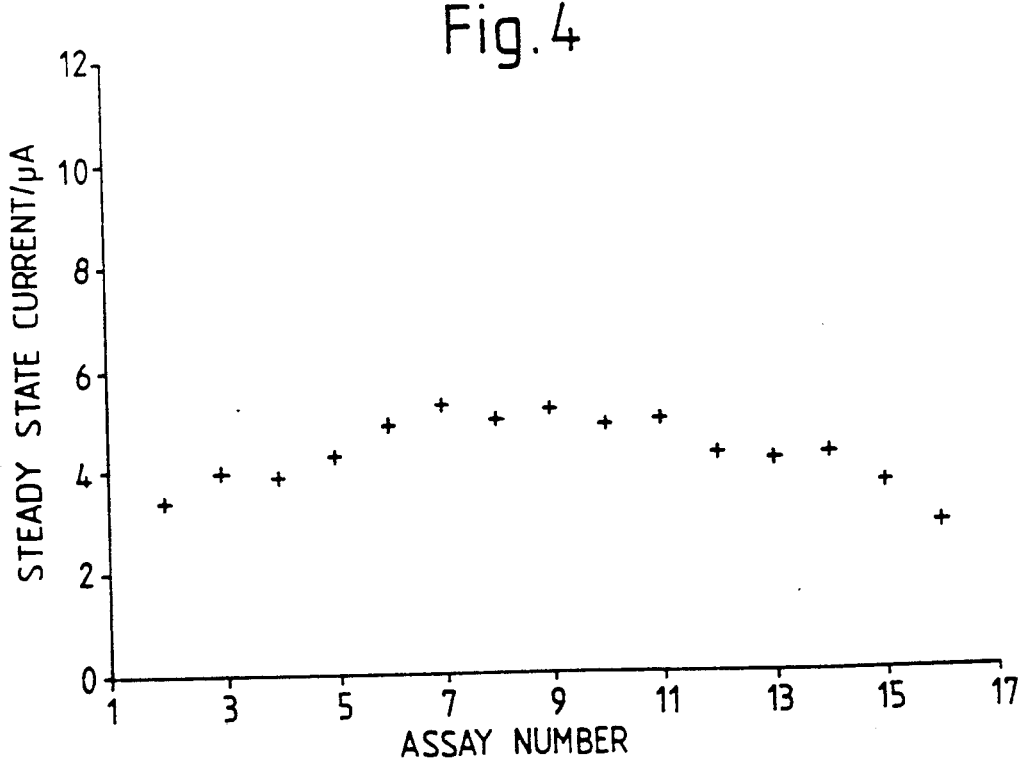
FIG. 4 shows the electrode response to p-cresol (100 µM) over sixteen consecutive assays.

The assay procedure outlined above was repeated with a final p-cresol concentration of 100 μM for a series of sixteen assays. The response of the electrode increased from 1.9 μA to 4.0 μA in the first three assays and then remained stable over the next eleven assays before starting to fall after assay number fourteen (FIG. 4).

STORAGE STABILITY

Eight electrodes were constructed with dry graphite blocks and their response to p-cresol (200 μM) was recorded. Half were then stored at room temperature and half at 5° C. At each temperature two electrodes were stored dry in bottles containing silica gel, and two were stored in chloroform. Their response to p-cresol (200 μM) was tested again after a few days and then after 7 weeks. The electrodes stored at room temperature showed an average loss of activity of 30% of the response after three days while those stored at 5° C. showed no significant decrease in their response to p-cresol (200 μM) (Table 1).

TABLE I

| Storage temp. (°C.) | Storage method | Initial response (μA) | Response after 3 days (μA) | Response after 48 days (μA) |
|---|---|---|---|---|
| Room temp. (20° C.) | Dry | 5.2 | 6.8 | 3.6 |
| | | 4.8 | 5.4 | 2.8 |
| | In CHCl$_3$ | 4.0 | 7.0 | 5.5 |
| | | 4.2 | 7.2 | 6.5 |
| 5° C. | Dry | 4.3 | 4.4 | 4.7 |
| | | 3.7 | 4.5 | 3.5 |
| | In CHCl$_3$ | 4.8 | 8.1 | 10.0 |
| | | 3.8 | 9.5 | 7.6 |

ELECTRODE SPECIFICITY

The response of a single electrode to a standard concentration (100 μM) of phenol, catechol, 4-methyl catechol, m- and p-hydroxy benzaldehyde, m-, p- and o-cresol, p-aminophenol and 4-chlorophenol was recorded. The electrode responded to all the phenols tested except o-cresol and p- and m-hydroxy-benzaldehyde (Table 2), indicating a potential use of the electrode as a phenol sensor.

TABLE 2

Response of the enzyme electrode to ten phenols (100 μM)

| Phenol | Electrode response (μA) |
|---|---|
| p-cresol | 5.6 |
| m-cresol | 4.7 |
| o-cresol | 0.0 |
| phenol | 6.4 |
| catechol | 8.6 |
| 4-methylcatechol | 6.7 |
| p-hydroxy-benzaldehyde | 0.0 |
| m-hydroxy-benzaldehyde | 0.0 |
| p-aminophenol | 2.4 |
| 4-chlorophenol | 3.1 |

REFERENCES

1. Yamane, T., Kojima, Y., Ichiryu, T. and Shimizu, S. (1988) Biocatalysis in microaqueous organic solvents. In Enzyme Engineering 9, Annals of the New York Academy of Science.
2. Turner, A. P. F., and Pickup, J. C. (1985), Biosensors 1, 85.
3. Cass, A. E. G., Davis G., Francis, G. D., Hill, H. A. O., Ashton, W. J., Higgins, I. J., Plotkin, E. V., Scott, L. D. L. and Turner, A. P. F. (1984), Anal. Chem., 56, 667–71.
4. Turner, A. P. F., Karube, I. and Wilson, G. S. (1987) Biosensors, Fundamentals and Applications. Oxford University Press.
5. Klibanov, (June 1986) Chemtech, p354.
6. Halling, P. J. (1987) Biotechnology Advances, 5; 47.
7. Kazandijan, R. Z. and Klibanov, A. M. (1985) Journal of the American Chemical Society, 107, 5448.
8. Murray, R. W., Ewing, A. G., and Durst R. A., (1987) Anal. Chem., 59, 379A.

We claim:

1. An enzyme electrode for use in a solvent selected from the group consisting of non-aqueous and microaqueous solvents, said electrode consisting essentially of a conductor, a hydrophilic support associated with the conductor, and an enzyme retained at said support, said conductor, said support and said enzyme being arranged such that when said electrode is inserted into the solvent, the solvent first contacts the enzyme and a bioelectrochemical reaction catalysed by said enzyme is effectable in the solvent.

2. An enzyme electrode according to claim 1 wherein the enzyme is retained at the support by their common hydrophilicity and not by covalent bonding.

3. An enzyme electrode according to claim 1 wherein the enzyme is a component of a member selected from the group consisting of a whole cell, a cell membrane and an organelle.

4. An enzyme electrode according to claim 1 wherein said support comprises a membrane of a polymeric compound which contains at least one of the group consisting of polar residues and inorganic membranes having polar groups at their surfaces.

5. An enzyme electrode according to claim 4 wherein said membrane is made of nylon.

6. An enzyme electrode according to claim 1 wherein the immobilised enzyme is a polyphenol oxidase.

7. A method for carrying out a bioelectrochemical reaction in a solvent selected from the group consisting of non-aqueous and microaqueous solvents, said method comprising contacting an electrode having an enzyme retained thereon with said solvent containing a substrate for said enzyme and allowing said substrate to undergo reaction at the electrode under the influence of said enzyme wherein said solution contacts the enzyme.

8. A method for the determination of an analyte present in a solution having a solvent selected from the group consisting of nonaqueous and microaqueous solvents said method comprising: introducing a non-aqueous or microaqueous solution to be analysed for said analyte into an electrochemical cell, said cell having an electrode at which an enzyme is retained; and measuring an electrical response of said cell; said response arising from a reaction involving said enzyme and said analyte and being relatable to the concentration of said analyte; wherein said solution contacts said enzyme.

9. A method according to claim 8 wherein said electrode comprises a conductor, a hydrophilic support associated with the conductor, and said enzyme being retained on said support.

10. A method according to claim 8 wherein the analyte is selected from the group consisting of a substrate or cofactor of said enzyme, a substrate convertible to a substrate or cofactor of said enzyme, a redox species capable of mediating electron transfer with the enzyme of said electrode and a substance convertible to a redox species capable of mediating electron transfer with the enzyme of said electrode.

11. A method according to claim 9 wherein the analyte is a phenol and the enzyme is a polyphenol oxidase.

12. A method according to claim 8 wherein the solvent is substantially immiscible with water.

13. A method according to claim 8 wherein the solvent is selected from the group consisting of hydrocarbons, organic halides, ethers, esters and mixtures thereof.

14. A method according to claim 8 wherein the solvent is saturated with water.

15. An electrochemical cell comprising an electrode at which an enzyme is retained and containing a solvent selected from the group consisting of non-aqueous and microaqueous solvents whereby a bioelectrochemical reaction is effectable in the solvent, catalysed by said enzyme, wherein said solvent is in contact with the enzyme.

16. An electrochemical cell according to claim 15 wherein the electrode comprises a conductor, a hydrophilic support associated with the conductor, and an enzyme retained at said support, said conductor, said support and said enzyme being arranged such that on insertion of the electrode into said solvent, said solvent first contacts the enzyme.

* * * * *